(12) United States Patent
Pines et al.

(10) Patent No.: US 7,061,237 B2
(45) Date of Patent: Jun. 13, 2006

(54) REMOTE NMR/MRI DETECTION OF LASER POLARIZED GASES

(75) Inventors: Alexander Pines, Berkeley, CA (US); Sunil Saxena, Pittsburgh, PA (US); Adam Moule, Albany, CA (US); Megan Spence, Zurich (CH); Juliette A. Seeley, El Cerrito, CA (US); Kimberly L. Pierce, El Cerrito, CA (US); Song-I Han, Berkeley, CA (US); Josef Granwehr, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 231 days.

(21) Appl. No.: 10/268,922

(22) Filed: Oct. 9, 2002

(65) Prior Publication Data

US 2003/0077224 A1 Apr. 24, 2003

Related U.S. Application Data

(63) Continuation-in-part of application No. 09/903,279, filed on Jul. 11, 2001, now Pat. No. 6,652,833.
(60) Provisional application No. 60/409,410, filed on Sep. 9, 2002, provisional application No. 60/399,041, filed on Jul. 25, 2002, provisional application No. 60/335,173, filed on Oct. 31, 2001, provisional application No. 60/335,240, filed on Oct. 31, 2001, and provisional application No. 60/218,549, filed on Jul. 13, 2000.

(51) Int. Cl.
 *G01V 3/00* (2006.01)

(52) U.S. Cl. ........................................ 324/304; 324/318
(58) Field of Classification Search ................ 324/319, 324/318, 309, 307, 300, 322; 600/410, 420, 600/422
See application file for complete search history.

(56) References Cited

U.S. PATENT DOCUMENTS 4,586,511 A    5/1986   Clark, Jr.
5,357,959 A *  10/1994  Fishman ..................... 600/420

(Continued)

FOREIGN PATENT DOCUMENTS

EP          0620 447 A2    4/1994

(Continued)

OTHER PUBLICATIONS

Bifone, A. et al.; "NMR of Laser–Polarized Xenon in Human Blood," Proc. Natl. Acad. Sci., vol. 93, pp. 12932–12936, Nov., 1996.
Overhauser, Albert W.; "Polarization of Nuclei in Metals," Physical Review, vol. 92, No. 2, pp. 411–415, Oct. 15, 1953.

(Continued)

*Primary Examiner*—Brij B. Shrivastav
(74) *Attorney, Agent, or Firm*—Joseph R. Milner

(57) ABSTRACT

An apparatus and method for remote NMR/MRI spectroscopy having an encoding coil with a sample chamber, a supply of signal carriers, preferably hyperpolarized xenon and a detector allowing the spatial and temporal separation of signal preparation and signal detection steps. This separation allows the physical conditions and methods of the encoding and detection steps to be optimized independently. The encoding of the carrier molecules may take place in a high or a low magnetic field and conventional NMR pulse sequences can be split between encoding and detection steps. In one embodiment, the detector is a high magnetic field NMR apparatus. In another embodiment, the detector is a superconducting quantum interference device. A further embodiment uses optical detection of Rb—Xe spin exchange. Another embodiment uses an optical magnetometer using non-linear Faraday rotation. Concentration of the signal carriers in the detector can greatly improve the signal to noise ratio.

72 Claims, 6 Drawing Sheets

U.S. PATENT DOCUMENTS

| | | | |
|---|---|---|---|
| 5,545,396 A | | 8/1996 | Albert et al. |
| 5,617,859 A | * | 4/1997 | Souza et al. ............... 600/420 |
| 5,642,625 A | | 7/1997 | Cates, Jr. et al. |
| 5,665,777 A | | 9/1997 | Fesik et al. |
| 5,688,486 A | | 11/1997 | Watson et al. |
| 5,698,401 A | | 12/1997 | Fesik et al. |
| 5,773,024 A | | 6/1998 | Unger et al. |
| 5,785,953 A | | 7/1998 | Albert et al. |
| 5,804,390 A | | 9/1998 | Fesik et al. |
| 5,846,517 A | | 12/1998 | Unger |
| 5,891,643 A | | 4/1999 | Fesik et al. |
| 5,989,827 A | | 11/1999 | Fesik et al. |
| 6,023,162 A | | 2/2000 | Johnson |
| 6,042,809 A | | 3/2000 | Tournier et al. |
| 6,043,024 A | | 3/2000 | Fesik et al. |
| 6,051,208 A | | 4/2000 | Johnson et al. |
| 6,071,494 A | | 6/2000 | Unger |
| H1968 H | * | 6/2001 | Bernstein ............... 600/410 |
| 6,288,261 B1 | | 9/2001 | Augeri et al. |
| 6,426,058 B1 | | 7/2002 | Pines et al. |
| 6,591,128 B1 | * | 7/2003 | Wu et al. ............... 600/422 |

FOREIGN PATENT DOCUMENTS

| | | |
|---|---|---|
| EP | 0 620 447 A2 | 10/1994 |
| WO | WO 95/27438 | 10/1995 |
| WO | WO 96/08234 | 3/1996 |
| WO | WO 96/28090 | 9/1996 |
| WO | WO 97/37239 | 10/1997 |
| WO | WO 98/18500 | 5/1998 |
| WO | WO 98/42383 | 10/1998 |
| WO | WO 00/25828 | 5/2000 |
| WO | WO 00/53229 | 9/2000 |

OTHER PUBLICATIONS

Rubin et al.; "Evidence of Nonspecific Surface Interactions Between Laser–Polarized Xenon and Myoglobin in Solution," PNAS, vol. 97, No. 17, pp. 9472–9475, Aug. 15, 2000.

Canceill et al.; "Synthesis and Exciton Optical Activity of D3–Cryptophanes," JACS, vol. 109, pp. 6454–6464, (1987).

Collet; "Cyclotriveratrylenes and Cryptophanes," in Tetrahedron Report Number 226, Tetrahedron, vol. 43, No. 24, pp. 5725–5759.

Kilenyi et al.; "Two New Abnormal Pathways in the Para–Claisen Rearragement of 2(Allyloxy)–and 2–(Crotyloxy)–3–Hydroxybenzaldehyde," JOC, vol. 56, pp. 2591–2594, (1991).

Wilchek et al.; "Applications of Aviden–Biotim Technology: Literature Survey," Methods in Enzymology, vol. 184, pp. 14–45.

Landon et al.; "Magnetization Transfer from Laser–Polarized Xenon to Protons Located in the Hydrophobic Cavity of the Wheat Nonspecific Lipid Transfer Protein," Protein Science, vol. 10, pp. 763–770, (2001).

Weber et al.; "Structural Origins of High–Affinity Biotin Binding to Streptavidin," Science, vol. 243, pp. 85–88, Jan. 6, 1989.

Rubin et al.; "Detection of a Conformational Change in Maltose Binding Proteins by 129–Xenon NMR" In press for JACS.

Brotin et al.; "129 Xenon NMR Spectroscopy of Deuterium–Labeled Cryptophane–A Xenon Complexes: Investigation of Host–Guest Complexation Dynamics," JACS, vol. 122, pp. 1171–1174, (2000).

Navon et al.; "Enhancement of Solution NMR and MIR with Laser–Polarized Xenon," Science, vol. 271, pp. 1848–1851, Mar. 29, 1996.

Tilton et al.; "NMR Studies of Xenon–129 with Myoglobin and Hemoglobin," Biochemistry, vol. 21, pp. 6850–6857, (1982).

Luhmer et al.; "Study of Xenon Binding in Cryptophane–A Using Laser–Induced NMR Polarization Enhancement," JACS, vol. 121, pp. 3502–3512, (1999).

Ginsburg et al.; "Temperature–Dependent Molecular Motions of Cholesterol Esters: A Carbon–13 NMR Study," Biochemistry, vol. 21, pp. 6857–6867, (1982).

Bowers et al.; "Exploring Surfaces and Cavities in Lipoxygenase and Other Proteins by Hyperpolarized Xenon–129 NMR," JACS, vol. 121, pp. 9370–9377, (1999).

Wolber et al.; "Hyperpolarized 129Xenon NMR as a Probe for Blood Oxygenation," Magnetic Resonance in Medicine, vol. 43, pp. 491–496, (2000).

Albert et al.; "Biological Magnetic Resonance Imaging Using Laser Polarized 129xe," Nature, vol. 370, pp. 200–201, Jul. 21, 1994.

Song, "NMR and MIR Using Laser–Polarized Xenon," Spectroscopy, vol. 14, pp. 726–733, Jul., 1999.

Ratcliffe, "Xenon NMR," Annual Reports on NRM Spectroscopy, vol. 36, pp. 123–200, (1998).

Walker et al.; "Spin–Exchange Optical Pumping of Noble–Gas Nuclei," Reviews of Modern Physics, vol. 69, No. 2, pp. 629–642, Apr., 1997.

Louie et al.; "In Vivo Visualization of Gene Expression Using MRI," Nature Biotechnology, vol. 18, pp. 321–325, Mar. 18, 2000.

Shuker et al.; "Discovering High–Affinity Ligands for Proteins: SAR by NMR," Science, vol. 274, pp. 1531–1533, Nov. 29, 1996.

Miyakaki et al.; "Fluorescent Indicators for Ca2+ Based on Green Fluorescent Proteins and Calmodulin," Nature, vol. 388, pp. 882–887, Aug. 28, 1997.

Checovich et al.; "Fluorescence Polarization–A New Tool for Cell Molecular Biloty," Nature, vol. 375, pp. 254–256, May 18, 1995.

Malmqvist; "Biospecific Interaction Analysis Using Biosensor Technolgoy," Nature, vol. 361, pp. 185–187, Jan. 14, 1993.

Smith et al.; "Intrcellular Calcium Measurements by 19F NMR of Fluorine–Labeled Chelators," PNAS, vol. 80, pp. 7178–7189, Dec., 1983).

Navon, G. et al.; "Enhancement of Solution NMR and MIR with Laser–Polarized Xenon," Science, vol. 271, pp. 1848–1851, Mar. 29, 1996.

McKim, Steven et al.; "Evidence of Xenon Transport Trhough the Gramicidin Channel: A 129–Xe–NMR Study," Biochimica et Biophysica Acta, vol. 1193, pp. 186–198, (1994).

Miller, Keith W. et al.; "Xenon NMR: Chemical Shifts of a General Anesthetic in Common Solvents, Proteins, and Membranes," Proc. Natl. Acad. Sci., vol. 78, No. 8, pp. 4946–4949, Aug., 1981.

Hall, Jason A. et al.; "Two Modes of Ligand Binding in Maltose–Binding Protein of *Escherichia coli*," Journal of Biological Chemistry, vol. 272, No. 28, pp. 17605–17609, Jul., 1997.

Sharff, Andrew J. et al.; "Refined 1.9A Structure Reveals the Mode of Binding of B–Cyclodextrin to the Maltodextrin Binding Protein," Biochmistry, vol. 52, No. 40, pp. 10553–10559, (1993).

Wolber, Jan et al.; "Spin–Lattice Relaxation of Laser–Polarized Xenon in Human Blood," Proc. Natl. Acad. Sci., vol. 96, pp. 3664–3669, Mar., 1999.

Gehring, Kalle et al.; "An NMR Study of Ligand Binding by Maltodextrin Binding Protein," Biochem. Cell Biol., vol. 76, pp. 189–197, (1998).

Sharff, Andrew J. et al.; "Crystallographic Evidence of a Large Ligand–Induced Hinge–Twist Motion Between the Two Domains of the Maltodextrin Binding Protein Involved in Active Transport and Chemotaxis," Biochmistry, vol. 31, pp. 10657–10663, (1992).

Szmelcman, Sevec & Schwartz, Maxime, "Maltose Transport in *Escherichia coli* K12," European Journal of Biochemistry, vol. 65, pp. 13–19, (1976).

Schwartz, Maxime, "In *Escherichia Coli* and *Salmonella Typhimurium*: Cellular and Molecular Biology;" The Maltose Regulon Neidhardt, F.C. et al. Eds.; American Society for Micorbiology, vol. 2, pp. 1482–1502, Washington, D.C., (1987).

Spurlino, John C. et al.; "The 2.3A Resolution Structure of the Maltose–or Maltodextrin– Binding Protein, A Primary Receptor of Bacterial Active Transport and Chemotaxis," The Journal of Biological Chemistry, vol. 266, No. 8, pp. 5202–5219, Mar. 15, 1991.

Labouriau, Andrea, et al.; "129–Xe NMR Spectroscopy of Metal Carbonyl Clusters and Metal Clusters in Zeolite NaY," J. Am. Chem. Soc., vol. 121, pp. 7674–7681, (1999).

Shilton, Brian H. et al.; "Conformational Changes of Three Periplasmic Receptors for Bacterial Chemotaxis and Transport: The Maltose–, Glucose/Galactose–and Ribose–Binding Proteins," J. Mol. Biol., vol. 264, pp. 35–363, (1996).

Walker, Thad G., "Spin–Exchange Optical Pumping of Noble–Gas Nuclei," Reviews of Modern Physics, vol. 69, No. 2, pp. 629–642, Apr., 1997.

Quillin, Michael L. et al., "Size Versus Polarizability in Protein–Ligand Interactions: Binding of Noble Gases Within Engineered Cavities in Phage T4 Lysozyme," J. Mol. Biol., vol. 302, pp. 955–977, (2000).

Prange, Thierry et al., "Exploring Hydrophobic Sites in Proteins with Xenon or Krypton," Proteins: Structure, Function, and Genetics, vol. 30, pp. 61–73, (1998).

Tilton, Robert F. et al., "Cavities in Proteins: Structure of a Metmyoglobin–Xenon Complex Solved to 1.9A," Biochemistry, vol. 23, pp. 2849–2857, (1984).

Schoenborn, Benno P. et al.; "Binding of Xenon to Sperm Whale Myoglobin," Nature, vol. 4992, pp. 28–30, Jul. 3, 1965.

Long, H.W. et al.; "High–Field Cross Polarization NMR from Laser–Polarized Xenon to a Polymer Surface," Journal of the American Chemical Society, vol. 115, No. 18, pp. 8491–8492, (1993).

Raftery D. et al.; "High–Field NMR of Adsorbed Xenon Polarized by Laser Pumping," Physical Review Letters, vol. 66, No. 5, pp. 584–587, Feb. 4, 1991.

Haase, A. et al.; "Flash Imaging. Rapid NMR Imaging Using Low Flip–Angle Pulses," Journal of Magnetic Resonance, vol. 67, pp. 258–266, (1986).

Mansfield, P.;, "Multi–Planar Image Formation Using NMR Spin Echoes," J. Phys. C: Solid State Phys., vol. 10, pp. L55–158, (1977).

Solomon, I.; "Relaxation Processes in a System of Two Spins," Physical Review, vol. 99, No. 1, pp. 559–565, Jul. 15, 1955.

Bartik, Kristin et al.; "129Xe and 1H NMR Study of the Reversible Trapping of Xenon by Cryptophane–A in Organic Solution," J. Am. Chem. Soc., vol. 120, pp. 784–791, (1998).

Faruqi, Tatjana R. et al.; "Structure–Function Analysis of Protease–Activated Receptor 4 Tethered Ligand Peptides," The Journal of Biological Chemistry, vol. 275, No. 26, pp. 19728–19734, (2000).

Sagane, Ryokichi et al.; "The Dependence of the 33–Mev Pi+ Production Cross Section on Atomic Number," Physical Review, vol. 92, No. 2, pp. 212–213, Oct. 15, 1953, Letters to the Editor.

Carver, Thomas R. et al.; "Experimental Verification of the Overhauser Nuclear Polarization Effect," Physical Review, vol. 102, No. 4, pp. 975–980, May 15, 1956.

Carver, Thomas R.; "Optical Pumping," Science, vol. 141, No. 3581, pp. 599–608, Aug. 16, 1963.

Noggle, Joseph H et al.; "The Nuclear Overhauser Effect," Chapter 1, pp. 4–43, Academic Press, (1971).

Tilton, R.F., Jr. et al.; "Nuclear Magnetic Resonance Studies of Xenon–129 with Myoglobin and Hemoglobin," Biochemistry, vol. 21, No. 26, pp. 6850–6857, 1982.

Bhaskar, N.D. et al.; "Efficiency of Spin Exchange Between Rubidium Spins and 129 Xenon Nuclei In a Gas," Physical Review Letters, vol. 49, No. 1, pp. 25–28, Jul. 5, 1982.

Happer, W. et al.; "Polarization of the Nuclear Spins of Noble–Gas Atoms by Spin Exchange with Optically Pumped Alkali–Metal Atoms," Physical Review A, vol. 29, No. 6, pp. 3092–3110, Jun., 1984.

Moschos, A. et al.; "Nuclear Magnetic Relaxation of Xenon–129 Dissolved in Organic Solvents," Journal of Magnetic Resonance, vol. 95, pp. 603–606, (1991).

Albert, Mitchell S. et al.; "Relaxation of 129–Xenon in Model Biological Systems: On Probing the Mechanism of General Anesthesia," 11th Annual Meeting Society of Magnetic Resonance in Medicine, pp. 2104, (1992).

Albert, Mitchell S. et al.; "129 Xenon Relaxation Catalysis by Oxygen," 11th Annual Meeting Society of Magnetic Resonance in Medicine, pp. 4710, (1992).

Raftery, D. et al.; "NMR of Optically Pumped Xenon Thins Films," Chemical Physics Letters, vol. 191, No. 5, pp. 385–390, Apr. 10, 1992.

Raftery, D. et al.; "Spin–Polarized 129 Xenon NMR Study of a Polymer Surface," Journal of Physical Chemistry, vol. 97, No. 8, pp. 1649–1655, (1993).

Bowers, C.R. et al.; "Cross Polarization from Laser–Polarized Solid Xenon to 13 CO2," Chemical Physics Letters, vol. 205, No. 2,3, pp. 168–170, Apr. 9, 1993.

Miller, J.B. et al.; "The NMR Chemical Shift of Xenon–129 Dissolved in Polymers," Macromolecules, vol. 26, No. 21, pp. 5602–5610, (1993).

Albert, M.S. et al.; "Biological Magnetic Resonance Imaging Using Laser–Polarized 129 Xenon," Letters to Nature, vol. 330, No. 21, pp. 199–201, (1994).

Song, Y.–Q. et al.; "Spin–Polarized 129 Xenon Gas Imaging of Materials," Journal of Magnetic Resonance vol. 115, pp. 127–130, (1995).

Albert, Mitchell S. et al.; "Measurement of 129 Xenon T1 in Blood to Explore the Feasibility of Hyperpolarized 129 Xenon MRI," Journal of Computer Assisted Tomography, vol. 19, No. 6, pp. 975–978, Nov.–Dec. 1995.

Driehuys, B. et al.; "Spin Transfer Between Laser–Plarized 129 Xenonnuclei and Surface Protons," Physics Letters A, vol. 184, No. 1, pp. 88–92, Dec. 27, 1993.

Driehuys, B. et al.; "Surface Relaxation Mechanisms of Laser–Polarized 129 Xenon," Physical Review Letters, vol. 74, No. 24, pp. 4943–4946, Jun. 12, 1995.

Service, Robert F., "Amplifying" "The Fine Details of Molecular Structure is a Gas," Science, vol. 271, pp. 1810, Mar. 29, 1996.

Wilson, Elizabeth K.; "Hyperpolarized Gases Set NMR World Spinning," Chemical Engineering News, vol. 74, No. 52, pp. 21–23, Dec. 23, 1996.

International Search Report from International Application No. PCT/US97/05166, Published as WO 97/37239, Oct. 9, 1997.

Middleton, Huner; "MR Imaging with Hyperpolarized 3–He Gas," Magnetic Resonance in Medicine, vol. 33, pp. 271–275, (1995).

Minagawa, Etsuo et al.; "Isolation and Characterization of a Thermostable Aminopepidase (Aminoopeptidase T) from Thermus Aquaticus YT–1, an Extremely Thermophilic Bacterium," Agric. Biol. Chem., vol. 52, No. 7, pp. 1755–1763, (1988).

Mizusawa, Kiyoshi et al.; "Production of Thermostable Alkaline Proteases by Thermophilic Streptomyces," Applied Microbiology, vol. 17, No. 3, pp. 366–371, Mar., 1969.

Roncari, G. et al.; "Thermophillic Aminopeptidases from Bacillus Stearothermophilus," pp. 45–61, Jul. 15, 1968.

Meriles, Carlos A. et al.; "Approach to High–Resolution Ex Situ NMR Spectroscopy," Science, vol. 293, pp. 82–85, Jul. 6, 2001.

Ackerman, Joseph H. et al.; "Mapping of Metabolites in Whole Animals by 31–P NMR Using Surface Coils," Nature, vol. 283, pp. 167–170, Jan. 10, 1980.

Stebbins, Jonathan et al.; "Nuclear Magnetic Resonance Spectroscopy in the Earth Sciences: Structure and Dynamics," Science, vol. 245, Issue 4915, pp. 257–263, Jul. 21, 1989.

Shachar, Frank et al.; "Voltage–Sensitive Magnetic Gels as Magnetic Resonance Monitoring Agents," Nature, vol. 363, pp. 334–336, May 27, 1993.

Hurlimann, M. et al.; "Spin Dynamics of Carr–Purcell–Meiboom–Gill–Like Sequences in Grossly Inhomogeneous B–O and B–1 Fields and Application to NMR Well Logging," Journal of Magnetic Resonance, vol. 143, pp. 120–135, (2000).

Blumich, B. et al.; "The NMR–Mouse: Constuction, Excitation, and Applications," Magnetic Resonance Imaging, vol. 16, No. 5/6, pp. 479–484, (1998).

Weitekamp, D. et al.; "High–Resolution NMR Spectra in Inhomogeneous Magnetic Fields: Application of Total Spin Coherence Transfer Echoes," Journal of the American Chemical Society, vol. 103, pp. 3578–3579, (1981).

Balbach, John et al.; "High–Resolution NMR in Inhomogeneous Fields," Chemical Physics Letters, vol. 277, pp. 367–374, (1997).

Hall, Laurance D. et al.; "Measurement of High–Resolution NMR Spectra in an Inhomogeneous Magnetic Field," Journal of the American Chemical Society, vol. 109, pp. 7579–7581, (1987).

Richter, Wolfgang et al.; "Imaging with Intermolecular Multiple–Quantum Coherences in Solution Nuclear Magnetic Resonance," Science, vol. 267, Issue 5198, pp. 654–675, Feb. 3, 1995.

Jerschow, Alexej; "Multiple Echoes Initiated by a Single Radio Frequency Pulse in NRM," Chemical Physics Letters, vol. 296, pp. 466–470, (1998).

Scharfnecker, Attila et al.; "Diffusion Measurements with the Aid of Nutation Spin Echoes Appearing After Two Inhomogeneous Radiofrequency Pulses in Inhomogeneous Magnetic Fields," Journal of Magnetic Resonance, vol. 148, pp. 363–366, (2001).

Ardelean, Ioan et al.; "The Nutation Spin Echo and Its Use for Locatilized NMR," Journal of Magnetic Resonance, vol. 146, pp. 43–48, (2000).

Levitt, Malcolm H.; "Composite Pulses," Historical Encyclopedia of NMR, Editors Grant & Harris, pp. 1396–1411, (1996).

Abragam, A.; "Thermal Relaxation in Liquids and Gases," Principles of Nuclear Magnetism, Oxford University Press, pp. 264–353, (1961).

Kleinberg, R.L. et al.; "Novel NMR Apparatus for Investigating an External Sample," Journal of Magnetic Resonance, vol. 97, pp. 466–485, (1992).

Andrew, E.R. et al.; "Nuclear Magnetic Resonance Spectra from a Crystal Rotated at High Speed," Nature–Letters to the Editor, pp. 1659, Dec. 13, 1958.

Andrew, E.R. et al.; "Possibilities for High–Resolution Nuclear Magnetic Resonance Spectra of Crystals," Discussions of the Faraday Society, High Resolution Nuclear Magnetic Resonance, vol. 34, pp. 38–42, (1962).

de Swiet, Thomas M. et al.; "In Situ Analysis of Fluids Contained in Sedimentary Rock," Journal of Magnetic Resonance, vol. 133, pp. 385–387, (1998).

Chmelka, B.F. et al.; "Some Developments in Nuclear Magnetic Resonance of Solids," Science, vol. 246, Issue 4926, pp. 71–77, Oct. 6, 1989.

Song, Yi–Qiao et al.; "Selective Enhancement of NMR Signals for X–Cyclodextrin with Laser–Polarized Xenon," Angw. Chem. Int. Ed. Engl., vol. 36, No. 21, pp. 2368–2370, Nov. 14, 1997, Abstract Only.

Augustine, Matthew P. et al.; "Low Field Resonance Images of Polarized Nobel Gases Obtained with a DC Superconducting Quantum Inerference Device," Applied Physics Letters, vol. 72, No. 15, pp. 1908–1910, Apr. 13, 1998.

Hall, Jason A. et al.; "Two Modes of Ligand Binding in Maltose–Binding Protein of *Escherichia coli*," Journal of Biological Chemistry, vol. 272, No. 28, pp. 17605–17609, Jul., 1997.

Bowers C.R. et al.; "Exploring Surfaces and Cavities in Lipoxygenase and Other Proteins by Hyperpolarized Xenon 129 NMR," Journal American Chemical Society, vol. 121, No. 40, pp. 9370–9378, (1999).

Diehl, P. et al.; "Nuclear Magnetic Relaxation of the 129 Xenon and 131 Xenon Isotopes of Xenon Gas Dissolved in Isotropic and Anisotropic Liquids," Journal of Magnetic Resonance, vol. 88, pp. 660–665, (1990).

Chawla et al. (1998), *In vivo* magnetic resonance vascular imaging using laser–polarized $^3$He microbubbles. *Proc. Natl. Acad. Sci. USA*, 95:10832–10835.

Luhmer, et al. (1999). Study of xenon binding in Cryptophane–A using laser–induced NMR polarization enhancement. *J. Am. Chem. Soc.*, 121:3502–3512.

* cited by examiner

REMOTE NMR/MRI DETECTION OF LASER POLARIZED GASES

CROSS-REFERENCE TO RELATED APPLICATIONS

This application is a continuation-in-part of U.S. application Ser. No. 09/903,279 filed on Jul. 11, 2001, now U.S. Pat. No. 6,652,833 which in turn claims priority from U.S. provisional application Ser. No. 60/218,549 filed on Jul. 13, 2000.

This application also claims priority from U.S. provisional application Ser. No. 60/399,041 filed on Jul. 25, 2002, from U.S. provisional application Ser. No. 60/335,173 filed on Oct. 31, 2001, from U.S. provisional application Ser. No. 60/409,410 filed on Sep. 9, 2002, and from U.S. provisional application Ser. No. 60/335,240 filed on Oct. 31, 2001.

This application is related to and incorporates by reference PCT International Publication No. WO 01/05803 A1 published on Jan. 24, 2002.

STATEMENT REGARDING FEDERALLY SPONSORED RESEARCH OR DEVELOPMENT

This invention was made with Government support under Contract No. DE-AC0376F00098, awarded by the United States Department of Energy. The Government has certain rights in this invention.

REFERENCE TO A COMPUTER PROGRAM APPENDIX

Not Applicable

BACKGROUND OF THE INVENTION

1. Field of the Invention

This invention pertains generally to nuclear magnetic resonance spectroscopy, and more particularly to an apparatus and method for NMR spectroscopy by spatially and temporally remote signal detection or optical detection.

2. Description of the Background Art

Nuclear magnetic resonance (NMR) has developed into a very versatile analytical tool for the study of molecular structures and surface features. However, NMR is a relatively insensitive detection method compared to others since the NMR signal depends on the population difference between two spin states. A number of approaches have been taken to increase the spatial, temporal and spectral resolution of NMR devices. One approach to increasing sensitivity is increasing magnetic field strengths since NMR sensitivity increases as the $7/4^{th}$ power of the strength of the magnetic field.

Another approach has been to improve the rf receiver coil size, geometry and component materials. It has been shown that the sensitivity of a detector coil is inversely proportional to the diameter of the coil. High temperature superconducting materials and cryogenically cooled detector coils have also improved the sensitivity of NMR devices.

One significant improvement in sensitivity was the discovery that NMR and MRI signals could be enhanced through the use of hyperpolarized Noble gases. Xenon and other Noble gases that are members of the zero group of the periodic table of elements, exhibit NMR characteristics that are highly sensitive to the chemical environment surrounding the atoms. The characteristic and highly sensitive chemical shift of $^{129}Xe$, and other noble gases has been widely used to probe the structure of molecules, microporous solids, such as zeolites and clathrates, and the surface features of membranes and other biological and non-biological materials. Recent improvements in the methods for producing hyperpolarized Noble gases have lead to many innovative NMR and MRI applications including medical imaging of the lungs and other parts of the body.

The technique typically used to produce hyperpolarized Noble gases involves the indirect transfer of angular momentum from optical photons to the nuclei of the noble gas molecules called "optical pumping and spin exchange." Optical pumping uses an alkali metal intermediary such as Rb, K, or Cs with a valence electron carrying the spin polarization to polarize the Noble gas. An intermediary is used because the polarization of photons cannot be directly transferred to the nuclear spins of the Noble gas atoms.

In the conventional setting, an alkali metal such as rubidium is vaporized and mixed with a Noble gas. The mixture is irradiated with circularly polarized laser light at the wavelength of the first principal resonance (i.e. its principal electric-dipole transition). For rubidium, the wavelength is 795 nm, for example. The alkali metal vapor absorbs a photon and the valence electron transitions from a ground state to an excited state.

The total angular momentum of both the ground state and the excited state of the alkali metal is $½$. Consequently, absorption of the circularly polarized light can only occur in the $-½$ ground state sublevel and not the $+½$ sublevel. Over time, essentially all of the Rb atoms are optically "pumped" into one sublevel because only one sublevel can absorb a photon. Under a modest magnetic field (10–80 Gauss), the cycling of alkali metal atoms between the ground and excited states can yield a substantial polarization of the atoms in a few microseconds. Thus, optical pumping creates electronic-spin polarization by selectively populating only one of the two possible spin states of the alkali-metal.

Exchange of the electronic orientation to the nuclear spin of the Noble gas takes place during binary collisions between the spin-polarized alkali metal atoms and the Noble gas atoms. During such collisions, the valence electron, through a hyperfine interaction, transfers angular momentum to the Noble gas nucleus causing a simultaneous nuclear and electronic spin flip. Thereafter, the alkali metal atom can absorb another photon and the process is repeated. In this manner, the nuclear polarization of the Noble gas can approach the level of the polarization of the irradiated alkali-metal vapor. Some production schemes provide a constant stream of hyperpolarized Noble gases that can be used in a magic angle spinning rotor or to circulate over or bubble through molecules in solution.

Hyperpolarized Noble gas atoms can also transfer spin polarization to the nuclei of atoms in sample molecules exposed to the gas. There are two primary techniques for the transfer of enhanced spin polarization from laser-polarized Noble gases to other nuclei such as protons that have been developed: (1) cross relaxation (SPINOE) and (2) cross polarization (CP).

The NMR signals of atoms in contact or close proximity to the hyperpolarized xenon are amplified due to the dipolar cross-relaxation and polarization transfer between the xenon and nuclear spins, a novel manifestation of the nuclear Overhauser effect termed SPINOE (spin-polarization-induced nuclear Overhauser effect). SPINOE also allows the transfer of spin polarization from laser-polarized gases to surface spins with no requirement for Hartman-Hahn matching of zero-field mixing. Solidification of the Noble gas is not required and consequently SPINOE can be carried out in a continuous flow mode and over a broader temperature range. Continuous flow of hyperpolarized Noble gas allows signal accumulation and therefore the exploration of surfaces with fewer spins or long relaxation times, as well as SPINOE under magic angle spinning.

Cross polarization, on the other hand, requires a static magnetic dipole interaction between the xenon spins and the nuclei that is the target of the transfer. With cross polarization, the xenon and the target nuclei are locked with simultaneous electromagnetic fields at two separate frequencies creating a quantum transition that allows the polarization to be transferred from the xenon to the target nucleus.

Hyperpolarized xenon and other noble gases can also be combined with a gas or fluid carrier that is chemically, biologically or materially compatible with the sample to be analyzed.

Poor sensitivity of conventional NMR detection coils at low fields has also been addressed with the use of superconducting quantum interference devices (SQUID), which have been used to obtain both spectra and imaging of laser polarized xenon for example. SQUID devices are presently one of the most sensitive detectors of magnetic flux. The AC or rf SQUID and the DC SQUID are the two main types of SQUID devices that have been developed. Generally, the SQUID device may be considered a flux to voltage converter consisting of a superconducting ring interrupted by one or more junctions called Josephson junctions and a large area flux antenna. Magnetic flux modulates the current passing through the Josephson junction.

However, SQUID devices exhibit instability in the presence of the pulsed magnetic fields that are necessary to prepare (encode) nuclear magnetization for detection. Consequently, these devices may be limited in their utility because of this instability.

Accordingly, there is a need for an apparatus and method for NMR/MRI spectroscopy that can optimize the encoding conditions and detection conditions without interference from ambient magnetic fields and overcomes many of the inherent limitations of traditional NMR devices. The present invention satisfies this need as well as others and generally overcomes the deficiencies of present devices and methods.

BRIEF SUMMARY OF THE INVENTION

The present invention is directed to an apparatus and method for Nuclear Magnetic Resonance or Magnetic Resonance Imaging that provides optimized NMR/MRI encoding coil geometries and conditions and optimized detecting methods and conditions through the spatial and temporal separation of the encoding and detecting steps and by the use of signal carrying sensors.

In general terms the invention comprises an encoder having a sample analysis vessel or chamber; a supply of polarized signal carrier atoms or molecules configured to discharge signal carrier sensors into the sample analysis vessel; and a detector configured to receive encoded signal sensors from the sample analysis vessel. The preferred signal carriers are hyperpolarized Noble gases, particularly xenon. Although xenon is preferred, essentially any gas or liquid that has a long polarization relaxation time can be used. A continuous source of laser polarized xenon through spin exchange with an alkali-metal such as rubidium in a low magnetic field is preferred.

In one embodiment, the source of the supply of signal carriers, the sample analysis vessel in the encoder and the detector chamber are operably interconnected with a continuous circulatory system including a pump. In another embodiment, the circulatory system includes a number of flow shut off valves allowing the control of the flow of signal carrier molecules between each of the system components. In another embodiment, the encoded signal carrier from the encoder can be enclosed in a tube or vessel and physically carried from one location to another.

According to another aspect of the invention, the signal carriers may be mixed with a liquid or gas that assists in the transportation or movement of the carrier molecules from the source of supply to the encoder and then to the detector. In MRI settings the transportation liquid is preferably chemically and biologically compatible with the sample or humans.

It can be seen that the spatial and temporal separation of the encoding and detecting steps allows the conditions of each step to be optimized depending on the subject of investigation. In one embodiment, the encoding can take place in a low magnetic field and the detecting step can be conducted in a high magnetic field NMR detector. In another embodiment, the encoding takes place in a high magnetic field coil and the detection takes place in a high magnetic field NMR detector. While high and low magnetic field encoding coils and detection coils are shown for illustration, it will be understood that essentially any combination of magnetic field strengths can be used in the encoding coil and detector coil embodiment of the invention.

In still another embodiment, the encoding takes place in a high or low magnetic field and detection is performed by a Superconducting Quantum Interference Device that directly measures magnetic flux.

In another embodiment, the detector is an optical detector that probes the build-up of spin polarization due to spin exchange between the encoded noble gas and an initially unpolarized alkali metal, such as rubidium, in the gas phase, which is exposed to the encoded noble gas. Optical detection using a magnetometer with nonlinear Faraday rotation is used in another embodiment of the invention.

According to another aspect of the invention, the pulse sequences that are typically needed can be split between the encoder and detector. The preferred sequence includes a period of time for the signal carriers to associate with the sample before a first 90° pulse in the encoding coil. A second 90° pulse in the encoding coil is applied after a dwell time. A third 9020 pulse with an FID is applied in the detecting coil after a travel time during which the encoded signal carriers have been transferred to the detector coil in one embodiment.

The invention also includes a method for remote NMR/MRI that generally comprises exposing a sample to a supply of polarized signal carriers and encoding NMR signals and then transferring the encoded carriers to a detector and detecting the encoded signals and analyzing the resulting spectra.

According to another aspect of the invention, the method of the invention may also include concentrating the encoded signal carriers in the detection analysis vessel or chamber by physical compression or thermal condensation, for example. Concentration of the encoded signal carriers increases the signal to noise ratios and provides a higher spin density.

According to another aspect of the invention, the coil geometry of the field coil in one embodiment of the detector is configured to maximize the filling factor. It is preferred that the greatest number of spins be provided within in the volume enclosed by the detector coil. A good filling factor is important in achieving the signal enhancement.

The use of an optical detector in one embodiment provides a more sensitive method of detection effectively amplifying the noble gas MNR/MRI signal thereby allowing detection of smaller sample sizes and the use of microdevices.

An object of the invention is to provide an apparatus and method that allows the spatial and temporal separation of the NMR signal preparation and detection steps.

Another object of the invention is to provide an apparatus and method that allows the optimization of the conditions of the encoding and detection steps independently of each other.

Another object of the invention is to provide an apparatus and method for imaging in the presence of susceptibility gradients using low magnetic fields and low frequency signals and detecting the signals at high magnetic field strengths.

Another object of the invention is to provide an NMR/MRI imaging apparatus that can be used in the presence of diamagnetic, paramagnetic and ferromagnetic materials and implants at low magnetic field strengths.

Yet another object of the invention is to provide a sensitive apparatus and method for NMR or MRI imaging that uses optical detection.

Another object of the invention is to provide a remote detection apparatus and method for NMR or MRI imaging that uses Superconducting Quantum Interference Devices for detection.

Still another object of the invention is to provide an apparatus and method for NMR spectroscopy that can functionally amplify signals from small sample quantities and accurately detect chemical shifts.

A further object of the invention is to take images as well as determine the travel time, flow and diffusion information over long distances.

Another object of the invention is to provide an apparatus and method that can provide remote NMR with detection magnets with poor field homogeneity.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings, which are for illustrative purposes only.

DETAILED DESCRIPTION OF THE INVENTION

Figure 1:
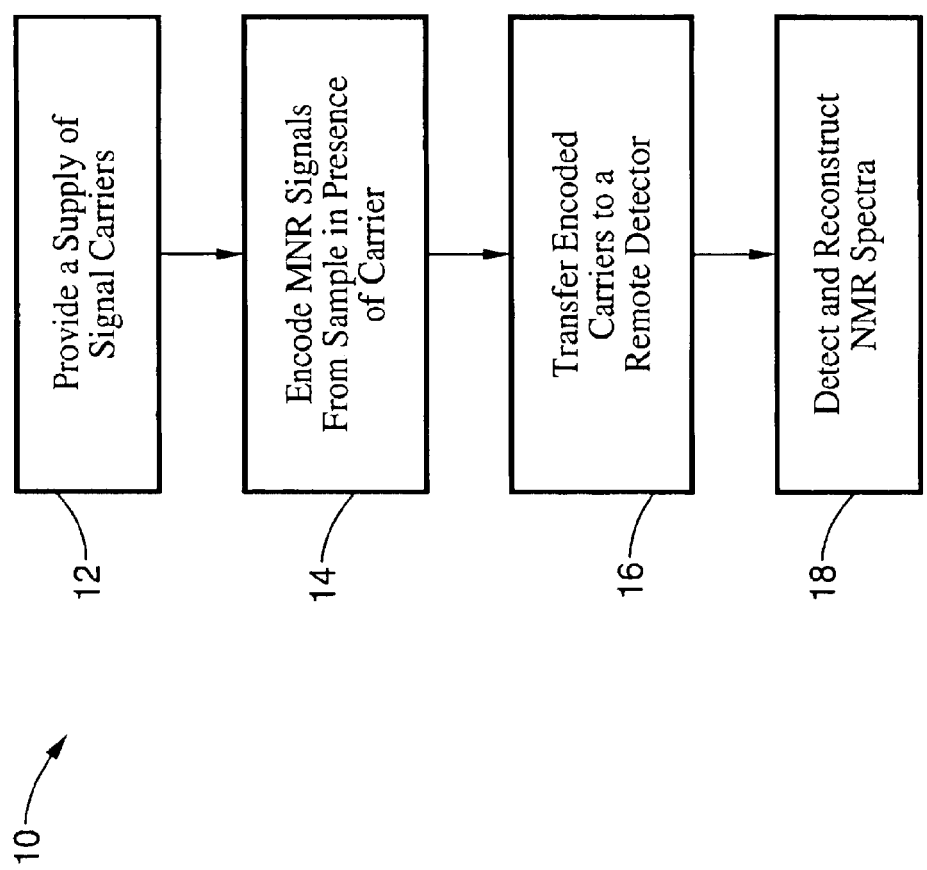
FIG. 1 is a flow diagram of the method of remote NMR detection according to the present invention.

Referring more specifically to the drawings, for illustrative purposes the present invention is embodied in the apparatus generally shown in FIG. 1 through FIG. 6. It will be appreciated that the apparatus may vary as to configuration and as to details of the parts, and that the method may vary as to the specific steps and sequence, without departing from the basic concepts as disclosed herein.

The remote detection apparatus according to the present invention allows the NMR signals from a sample to be encoded and detected in separate locations, environments, and times through the use of signal carrying sensors (signal carriers), an encoding coil and a remote detector.

There are several advantages to separating the encoding and detection steps in an NMR or MRI procedure. The NMR signals from a subject or sample can be amplified if the detection field is higher than the encoding field, the filling factor is more favorable, or the encoded carrier molecules are concentrated in the detection coil. The NMR signals may also be qualitatively amplified by using detection devices that are more sensitive than conventional high field NMR or MRI detectors.

One obvious advantage to separate encoding and detection steps is that the conditions of the sample and encoding can be manipulated independently from those conditions for detection allowing the optimal conditions for each to be chosen. There are several factors that contribute to the strength of the NMR signal including the size and geometry of the rf coil, the concentration and volume of the sample, the filling factor, the nuclear polarization, the nuclear precession frequency, and the line width of the resonance. Since the resolution of the encoded NMR signal is determined by the characteristics of the encoding magnet, the characteristics of the encoding apparatus including the magnetic field and coil geometries can be optimized. For example, the resolution of imaging information can be improved by removing high field susceptibility artifacts from the image by lowering the encoding field. Since susceptibility differences in a sample scale with the static field, resolution can be improved by imaging at lower fields. However, there is also a cost in signal to noise. Low fields, as referred to herein, typically range from approximately 0 Tesla to approximately 1 Tesla.

Likewise, the detection efficiency scales linearly with the detection frequency indicating that a higher field for detection is optimum. High fields refer to a magnetic field that is greater than approximately 1 Tesla. A detector that is remote from the encoder allows a susceptibility related resolution gain by imaging at a lower field with no cost in signal to noise because the signal is still detected at high field.

Additionally, the detection magnetic field could be inhomogeneous and still yield the resolution determined by the encoding field. This could be especially useful for settings in which the high field signal is unsteady such as in a high field magnet laboratory or simply an inexpensive un-shimmed magnet is all that is available. Indeed, the majority of the cost of a high field magnet system comes from difficulties in shimming and the need to cryogenically cool the magnets. If detection homogeneity requirements are reduced, detection can be conducted using permanent magnets or higher temperature electromagnets. Consequently, the costs associated with detection can be greatly reduced with the use of un-shimmed detection devices operating at comparatively lower magnetic field strengths and homogeneities.

Other detection methods do not require the use of high encoding fields including SQUID and optical detection.

Since both of these techniques measure magnetization directly they do not rely on a high field to induce a high precession frequency and thus high signal. Using these methods the field requirements would be determined by the needs of the signal carrier to maintain its polarization.

Additionally, high magnetic fields can be used around the sample to resolve small chemical shift differences during encoding and then directly detected with either high or low magnetic fields. Accordingly, it can be seen that the coil geometries and sampling conditions in encoding coil and detector can be optimized with remote detection.

Remote detection may also be advantageous in certain medical applications such as imaging of the lungs. For example, a patient may be given a quantity of laser polarized xenon by inhalation which is adsorbed on to the lung tissue. It would be difficult to detect the adsorbed xenon signal with conventional MRI because the filling factor of the huge coil wrapped around the body would be so poor. With the remote detection scheme of the present invention, the xenon chemical shift and location would first be encoded by rf pulses and magnetic field gradients around the body and then exhaled and transported to an optimized detector where the signal could be detected. Thus, if the gas from the lungs were to be collected into coils with an excellent filling factor the S/N could be much improved. Accordingly, the filling factor can easily be improved for void space NMR and MRI with the spatial and temporal separation of the encoding and detection steps.

Similarly, a patient would inhale a volume of xenon while in a conventional MRI apparatus and a sample could be encoded. The path of the encoded blood can be traced non-invasively. Likewise, the circulation of blood in parts of the body may be tracked through vascular restrictions and the like with polarized Xe dissolved in a compatible liquid and introduced through a catheter for example.

Similarly, low field encoding will allow imaging in the presence of diamagnetic, paramagnetic or ferromagnetic materials. For example, patients with medical implants made from magnetic materials risk the movement of such implants when exposed to strong magnetic fields. Consequently, these patients are presently deprived of the benefits of conventional MRI imaging. The separation of the encoding and detecting steps allows encoding at very low fields while detection is performed at high fields.

Another advantage is that the signal to noise (S/N) ratio for small concentration samples can be substantially improved by concentrating the encoded signal carriers in the detector. A gaseous sample of signal carrier sensors can be concentrated by either condensation or pressurization or by chemical concentration methods. Additionally, all encoded signal carrier sensors can be concentrated by improving the filling factor.

Alternative methods of detection may also be employed by the use of spatially separated encoding and detection steps. For example, the limitations experienced by SQUID devices in the presence of pulsed magnetic fields can be overcome by removing the detector from proximity to the NMR encoding coils or other sources of interfering magnetic fields. The pulses required to encode the spins from the subject sample are sufficiently removed from the detector so that the sensitive SQUID detector can be used.

Likewise, optical detection methods via Rb-Xe spin exchange or an optical magnetometer using nonlinear Faraday rotation may also be used in the alternative to traditional NMR coil detection. These methods detect magnetization directly so that the field requirements are greatly reduced.

Accordingly, remote detection may allow one to gain spatial or spectroscopic information from signals that were previously too small to be measured and now become accessible. Ultra-low field encoded samples, biological tissue and low concentration sites in materials may now be susceptible to spectroscopy with remote detection. Thus, performing NMR or MRI at ultra-low magnetic fields will minimize the effects of susceptibility gradients in a sample. Therefore, spectroscopy and imaging of highly heterogeneous samples or samples in the presence of metals may now be possible.

Turning now to FIG. 1, a flow diagram of one embodiment of the method 10 according to the present invention is generally shown. In this embodiment, a supply of signal carriers, preferably hyperpolarized xenon, is provided at block 12. The signal carriers are directed to a chamber containing a sample in an encoder and NMR signals are encoded at block 14. The encoded-signal-carrying atoms or molecules are then transferred from the encoder to a remote detector at block 16 where the signal carriers can be concentrated and detected using any method capable of detecting the encoded signal at block 18.

Figure 2:
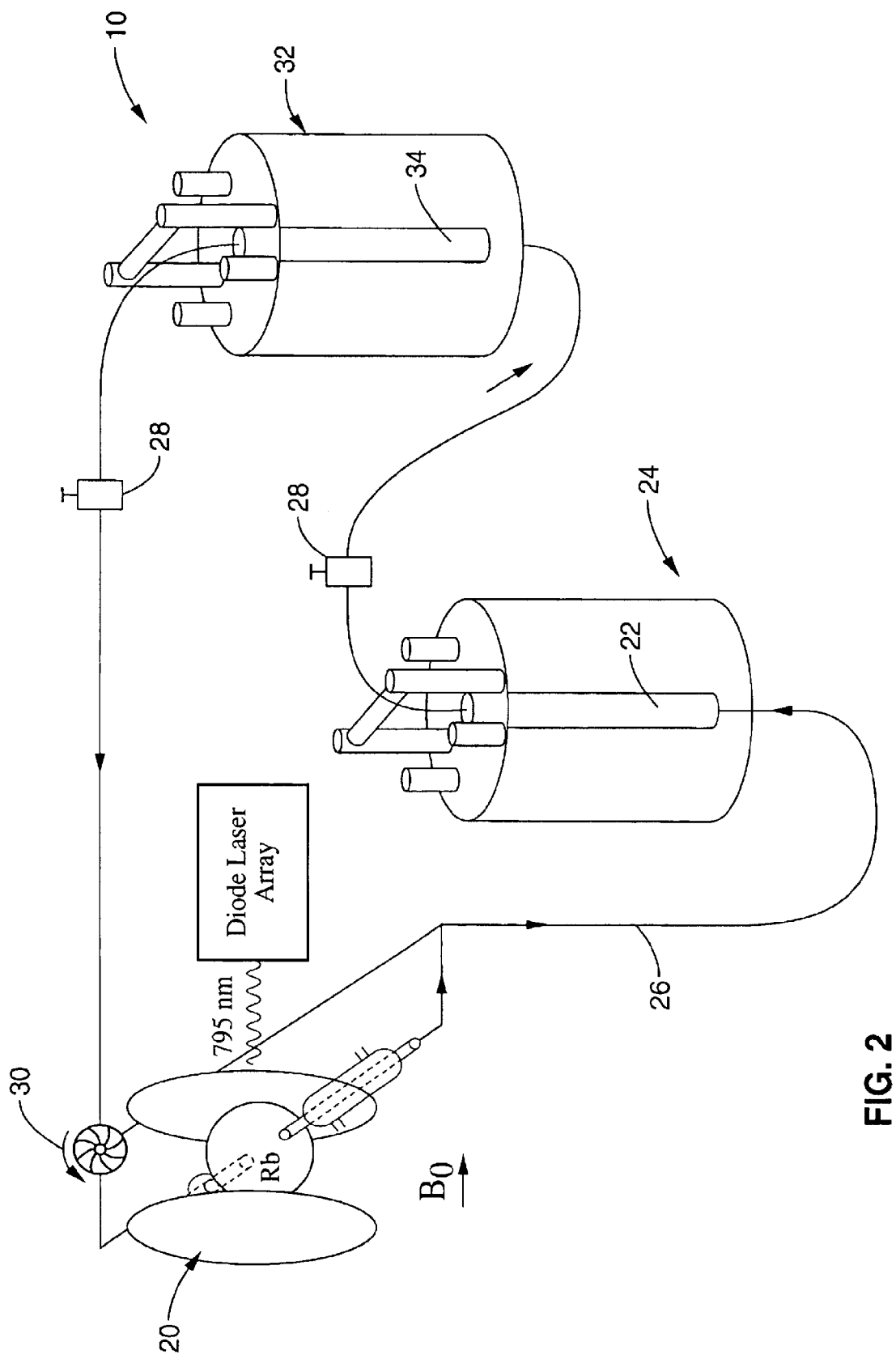
FIG. 2 is a schematic diagram of one embodiment of the apparatus of the present invention with a high magnetic field NMR encoder and a remote high field detector in a closed system.
Figure 3:
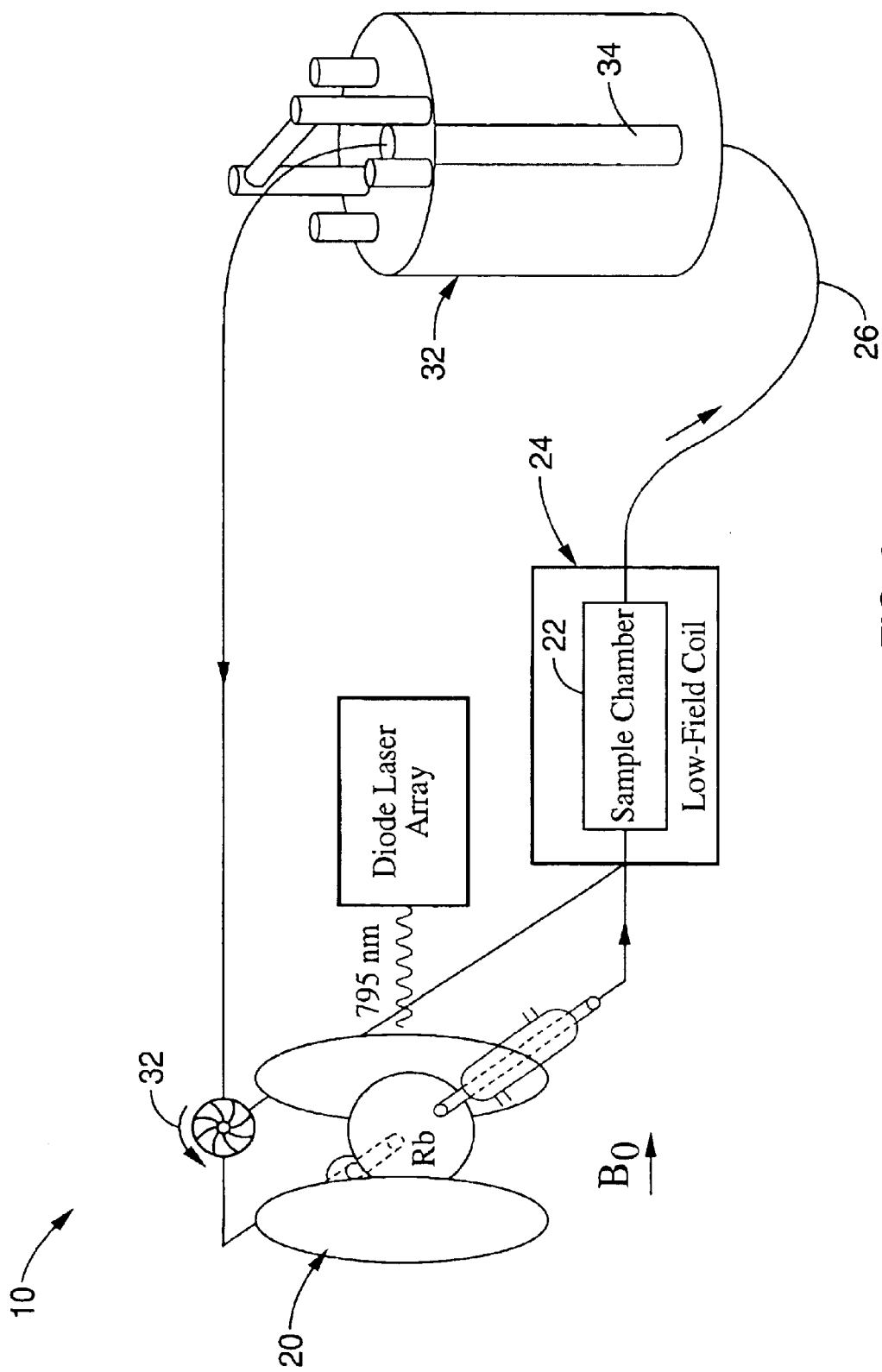
FIG. 3 is a schematic diagram of one embodiment of the apparatus of the present invention with a low magnetic field NMR encoder and a remote high field detector in a closed system.
Figure 4:
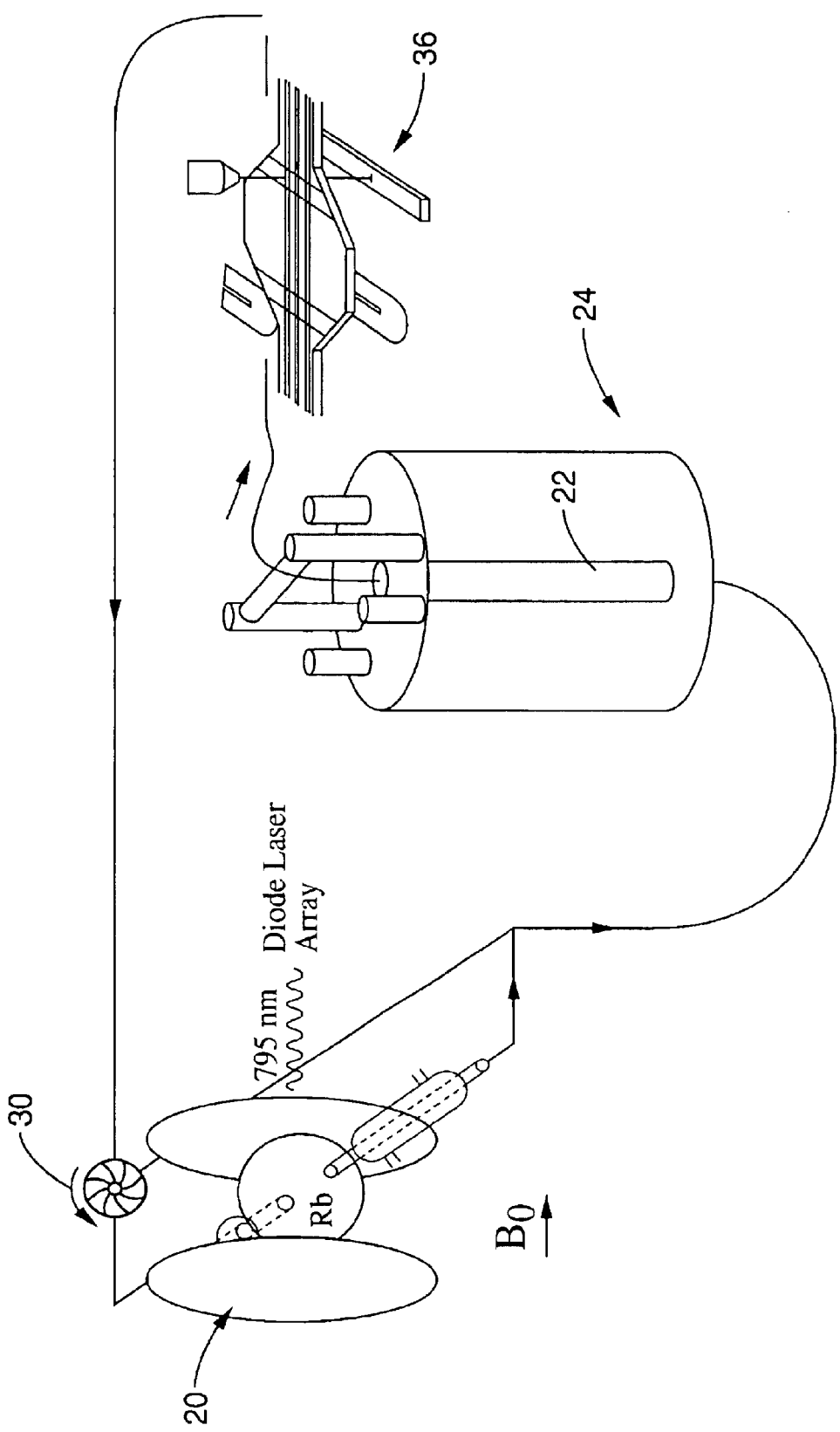
FIG. 4 is a schematic diagram of one embodiment of the apparatus of the present invention with a low magnetic field NMR encoder and an alternative optical detector in a closed system.

Referring also to FIG. 2, FIG. 3 and FIG. 4, alternative embodiments of a closed flow system of the apparatus can be seen. In the embodiment shown in FIG. 2, the supply of signal carriers is produced in a hyperpolarizer 20 that is connected with suitable tubing 26 to a sample chamber 22 that preferably resides in an encoder 24. The system of tubing preferably has one or more valves 28 that will allow the selective flow of signal carriers through the various components in the system.

The system in the embodiment shown in FIG. 2, FIG. 3 and FIG. 4, has a pump 30 that will provide a continuous flow of signal carriers and will also create pressure in the system. While a closed system is preferred, it will be understood that an open system using a batch method is also contemplated. In an open system embodiment, the signal carrier atoms are transported in a batch from the hyperpolarizer 20 to the encoder 24 and finally to the decoder 32. Another open system embodiment uses continuous flow from the pumping cell through the encoding and detection coils and then out to the atmosphere.

Referring specifically to block 12 of FIG. 1, a supply of signal carrying sensors is provided. It has been shown through experiments involving nuclei with long $T_1$ times, pre-polarizing fields, or small tip angles (Flash), that once a volume of spins has gained a certain polarization, the signal can be stored and later detected at any time until the sample has been fully saturated or longitudinally relaxed. A signal carrier is defined herein as a magnetically active-nucleus containing species atom or molecule that preferably has the capability of polarization transfer with a sufficiently long relaxation time as well as the capability of associating with protons and other atoms in a sample. The signal carrier is preferably chemically inert but may be chemically or biologically compatible with the sample to be analyzed. Hyperpolarized noble gases are the preferred signal carrying sensors in the present invention. Noble gases such as $^{129}Xe$ are particularly useful in NMR because the Xe nucleus has a spin of ½.

The signal carriers may be gaseous or liquid although gaseous carrier atoms are preferred. Additionally, gaseous signal carriers may be dissolved or mixed with liquids or other gases. These liquids or gases preferably facilitate the transfer through the encoder to the decoder through the system. For example, it has been shown that hyperpolarized $^{129}$Xe gas can be mixed with liquids or gases and maintain the polarization for several hours. Such liquids may include, but are not limited to water, saline solution, isotonic buffers, lipid emulsions, organic solvents, fluorocarbon blood substitutes including aqueous perfluorocarbon emulsions and other medically safe media. In non-medical applications, any liquid or gas that does not substantially interfere with the polarization of the signal carrier molecules may serve as a transportation media. Liquids that are capable of dissolving large quantities of xenon and other noble gases are especially preferred.

There are a number of methods and devices for producing and accumulating hyperpolarized noble gases known in the art. Recent advances in the technology for the production of hyperpolarized noble gases including high power laser arrays and continuous flow optical pumping cells allow the production of large quantities of hyperpolarized gases that can be used immediately or produced and stored for later use. The typical and preferred method for producing hyperpolarized gas is the optical pumping spin exchange method using an alkali-metal intermediary to polarize the preferred noble gas.

Referring now to block 14 of FIG. 1, FIG. 2, FIG. 3 and FIG. 4, once as supply of signal carriers is produced and accumulated, the carriers are introduced into a chamber 22 holding the sample. The sample chamber 22 is preferably located in an encoder 24. The preferred encoder 24 comprises a high resolution NMR spectrometer providing a homogeneous magnetic field. In the sample chamber 22, magnetic field gradient and radio frequency pulses are preferably used to encode spatial or spectroscopic information and prepare the signal carrier molecule spins for detection. The flow of signal carrier molecules is preferably stopped during encoding and detection steps with valves 28.

It can also be seen that the spatial separation of the encoding apparatus from the detecting apparatus allows optimal conditions for encoding and detection to be selected including coil geometries and magnetic field strengths. For example, the encoding takes place in a high magnetic field and detection takes place in a high magnetic field in the embodiment seen in FIG. 2 and shown in Example 1.

Alternatively, in the embodiment seen in FIG. 3 and shown in Example 2, the encoding takes place in a low magnetic field and detection takes place in a high magnetic field. In another embodiment, the encoding takes place in a high magnetic field and the detection takes place in a low magnetic field. Although a high and low field encoding and high and low field detection embodiments are shown for illustration, it will be understood that the encoding fields and detecting fields may be provided at essentially any field strength.

In addition, although encoding is preferred within a homogeneous magnetic field, it will be understood that encoding may take place in inhomogeneous fields under some circumstances. For example, a portable apparatus may be used where the signal was encoded by inhomogeneous surface coils out in the field, such as with porous materials containing oil or the like, and then detected with a better filling factor to enhance signal to noise that one would get with a surface coil.

Furthermore, since the sample is encoded at one location and the signal detected at another location, traditional pulse sequences known in the art can be divided temporally and spatially. In the preferred embodiment, the hyperpolarized $^{129}$Xe carrier molecules are delivered to the sample in chamber 22 and the flow of gas is stopped for a time:

$$\tau_s = \tau_{eq} + \tau_{90} + N*dw2 + \tau_{90} + \tau_{eq2}$$

in the encoding coil 24 to allow an equilibration time $\tau_{eq}$ before a first pulse and a mixing time $\tau_{eq2}$ after a second pulse. The preferred encoding step comprises a series of two 90° pulses divided by a variable dwell time N*dw2. The first pulse begins precession in the x-y plane and the second stores the magnetization in the +/−z direction. Since a phase difference develops between the rotating magnetization and the carrier frequency, the amplitude of the magnetization rotated into the +/−z direction varies as a function of the phase difference.

It will be understood that different pulse schemes may be used for the high field and low field encoding. For example, at high field, normal rotating frame pulses may be applied. In this embodiment, the amplitude of the signal stored by the second encoding pulse is proportional to the development of phase with respect to the rotating frame carrier frequency. Since the magnetization of the carrier molecules from the encoder 24 is stored as an amplitude, there is no phase information stored and therefore no quadrature. If the second low field pulse is alternated between sin and cos in the rotating frame, quadrature may reconstructed by acquiring the real and imaginary FID's separately during detection.

At low field, in one embodiment all of the pulses in the encoding coil 24 begin and end with x-direction zero phase in the lab frame. The time between pulses may be set arbitrarily, meaning that the second pulse stores an amplitude proportional to the development of phase with respect to the x-direction in the lab frame. In this case the actual precession of the magnetization is mapped out in the lab frame. When the dwell time is too long to meet the Nyquist condition an apparent frequency is recorded.

$$\omega_{apparent} = \text{MOD}(dw2*\omega_{Larmor})/dw2$$

Referring now to block 16 of FIG. 1, the encoded signal carrier molecules are transferred in a traveling time $T_t$ from the encoder 24 to the detector 32 with a detection chamber 34 as shown in FIG. 2. The encoded magnetization reaches the detector over a time period Tt+n*Td. Where $T_t$ is defined as the shortest time in which the magnetization shows variation and $T_d$ is the time between detections. $T_d$ is preferably chosen to be long enough so that the gas in the detection coil exchanges by greater than 95%. The time between encoding and detection steps may typically range between milliseconds to several hours or until the signal carrier sample has been fully saturated or longitudinally relaxed.

In an alternative embodiment, the encoded signal carriers are collected in a container and transported to detector 32. It can be seen that simply removing the carrier molecule before detection allows physical compression or thermal compensation which can concentrate the encoded signal carrier molecules up to three orders of magnitude in the detector, yielding a higher spin density and coil filling factor leading to greatly improved signal to noise ratios.

It has been seen that the amplitude of the signal detected after a 90° pulse at the detector 32 is constant if the encoding step at encoder 24 is excluded. Additionally, a single 90° pulse at encoder 24 causes the magnetization to precess and in the case of hyperpolarized $^{129}$Xe also destroys the high polarization. The travel time $T_t$ between locations may be experimentally determined by inverting the magnetization in the encoding coil 24 using an adiabatic sweep pulse or a hard 180° pulse. The inverted magnetization mixes with un-encoded $^{129}$Xe as it flows through sealed tubing 26.

Once in the detection coil at block 18 of FIG. 1, the amplitude of the encoded magnetization is preferably detected using a third 90° pulse in the embodiment shown. The length of N*dw2 at the encoder 24 determines the amplitude of the z-direction magnetization when it is detected as a FID at detector 32. The amplitude variation due to changing dw2 is the signal encoded at the encoder 24. The variation of N*dw2 at the encoding coil indirectly maps out the encoded FID as part of a 2D experiment.

A series of acquisitions are preferably made then in the detection coil at detector 32 in the embodiment shown in FIG. 2. The variation in the amplitude of the gas peak in this series of spectra is due entirely to the cancellation in total polarization due to the inverted magnetization that was in the encoder 24 at $T_t$=0 s.

Figure 5:
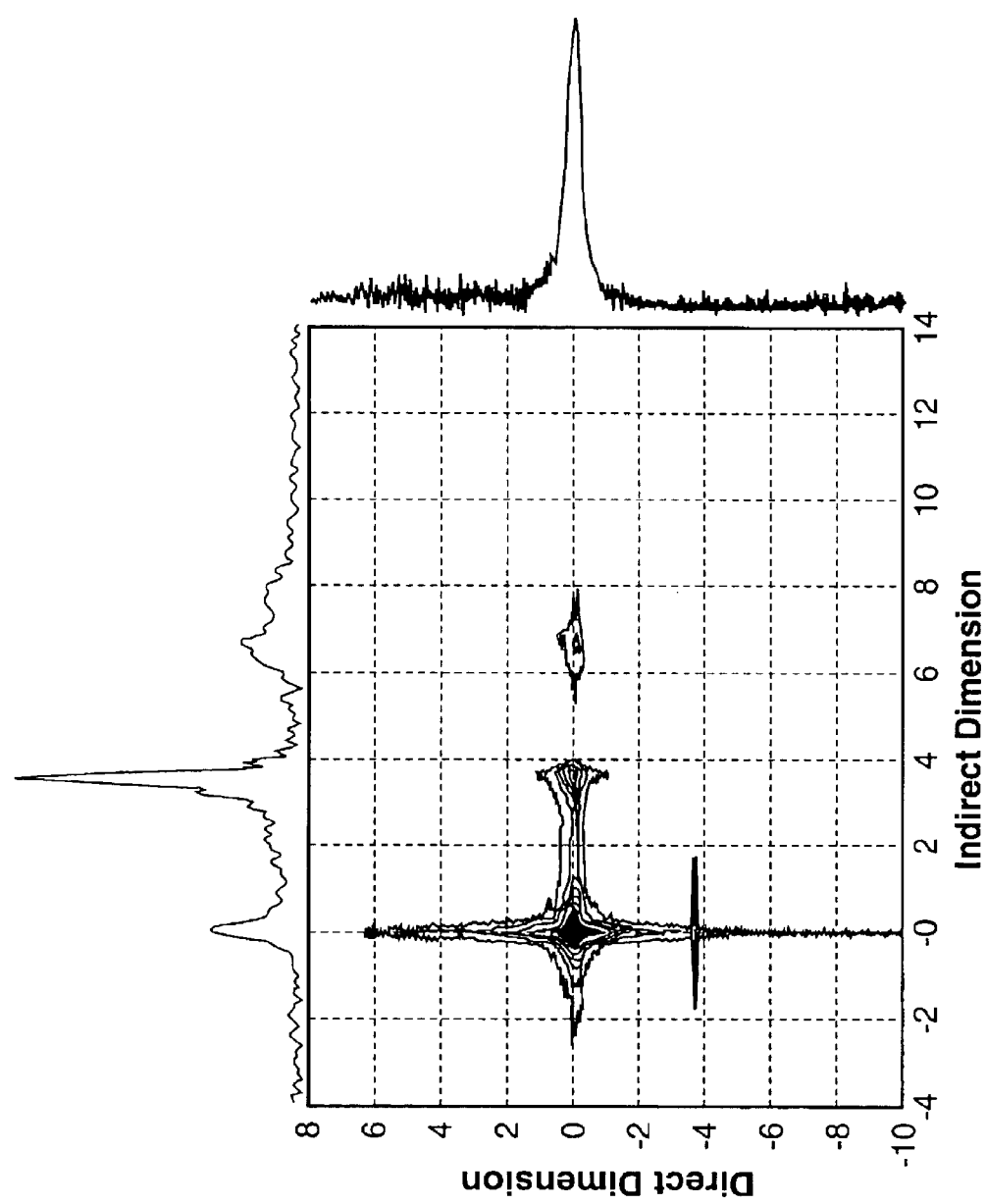
FIG. 5 is a two dimensional graph of the remote detection of chemical shift of xenon.
Figure 6:
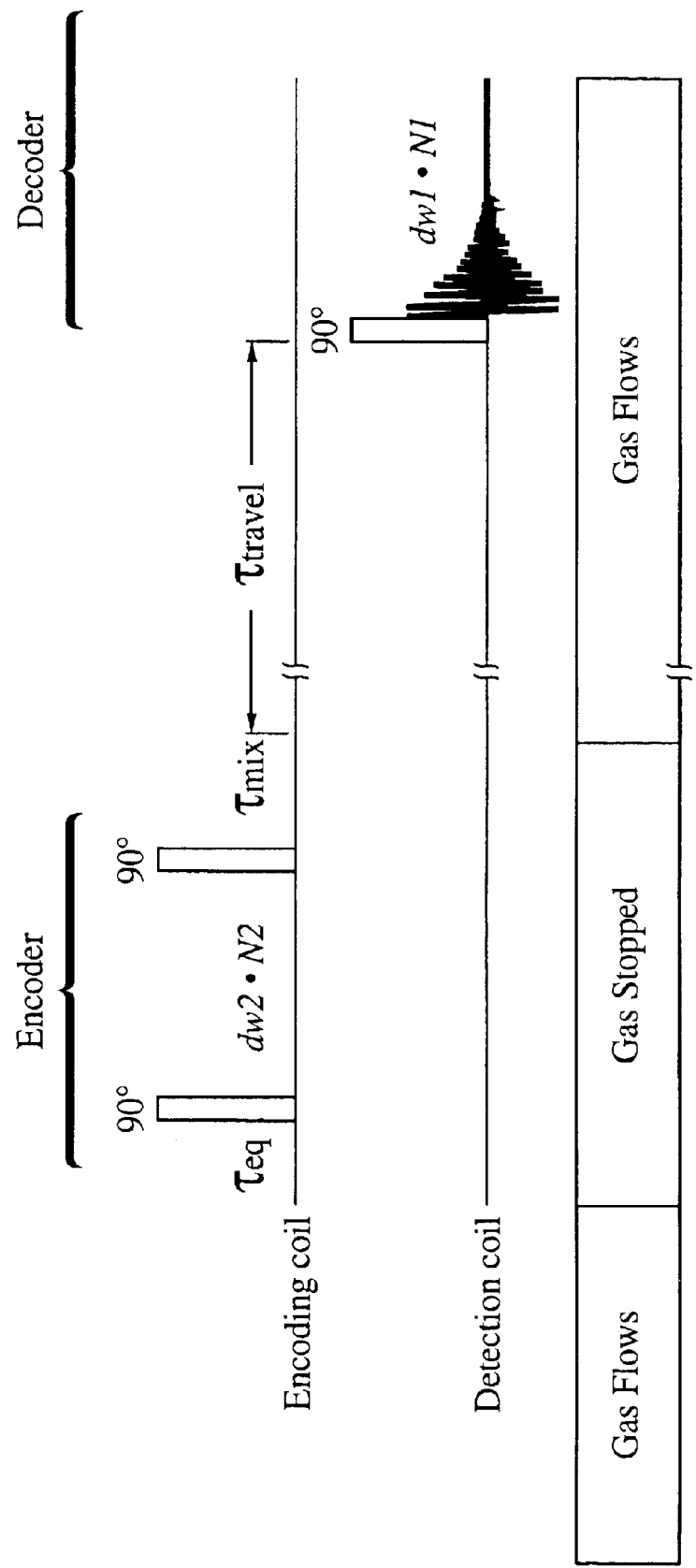
FIG. 6 is a pulse sequence for a low magnetic field encoding and high magnetic field detection shown in FIG. 3 according to the present invention.

In remote detection procedures, the data is preferably two dimensional and taken point by point as seen in FIG. 5, for example. An amplitude is stored for each encoding step, and, after traveling to the detection coil 32, is acquired as a single point in the indirectly encoded spectrum. The polarization resulting from a given series of encoding pulses and evolution times is stored along the z-axis for its intensity to be detected in the detector 32. Signal intensity may be measured for each pulse strength and evolution time, allowing the effect of the pulses and evolution to be recorded multi-dimensionally. The use of a point-by-point detection scheme will produce a remotely detected spectrum will have one more dimension of data than the equivalent directly detected spectrum.

Amplification of the signal in the detection coil by concentration or by detecting at a high field will also permit longer transportation and procedure times as well as allow signal averaging. In one embodiment, a selective pulse centered about the functionalized-xenon resonances is used to allow signal averaging of the functionalized-xenon peaks. Between saturations the mixing time ($\tau_{mix}$) allows for the replenishment of functionalized-xenon signal by exchanging saturated spins with excessive polarized xenon that has been dissolved in water. One preferred pulse is an EBURP1 pulse designed to selectively saturate magnetization.

Because the sample is not required to fit within the detection coil, optimum coil geometries for the detector 32 can be achieved in the embodiments shown in FIG. 2 and FIG. 3. Furthermore, alternative detection methods can be utilized because the detector 32 is separated in space and time from the encoder 24. For example, Superconducting Quantum Interference Devices (SQUIDs) can be used to directly detect magnetic flux rather that the rate of change of flux. SQUIDs are very sensitive detectors of magnetic fields that generally comprise a superconducting loop with a plurality of Josephson junctions that are typically formed by a very thin insulating barrier through which electron pairs can tunnel. In the presence of a magnetic field, the electrical current in the superconducting material will change as strength of the encountered magnetic field changes thereby providing an easily measurable voltage change corresponding with a change in the magnetic field. Predictably, ambient magnetic fields interfere with the accurate function of SQUID devices. Accordingly, a SQUID detector that is spatially isolated from the high magnetic fields of encoding coils will not experience the interference of the encoding coils or other stray magnetic fields.

Referring also to FIG. 4, an optical detector 36 and similar methods can be used in the alternative of a high field NMR detector or a SQUID device. In the embodiment shown in FIG. 4, an optical detection apparatus 36 generally includes a detection chamber that receives polarized and encoded signal carriers from the encoder 24 and contains a volume of a vaporized alkali metal, preferably rubidium. The signal carriers, preferably xenon, create a rapid spin-exchange with the rubidium perturbing the polarization of the rubidium. The resulting rubidium polarization indirectly reports the $^{129}$Xe polarization and can be directly detected optically. Since optical detection is many orders of magnitude more sensitive than the NMR signal, especially for low $^{129}$Xe concentrations, a large amplification of the Xe NMR/MRI signal is obtained. Alternatively, an optical magnetometer using nonlinear Faraday rotation may also be used.

In the case of optical detection, a multi-dimensional procedure need not be conducted. Since the magnetization is measured directly, a 90° pulse does not need to be applied and there is no FID to detect in the direct dimension. Instead, the amplitude of the magnetization is measured directly and supplies one point in the point-by-point encoded spectrum. Likewise, a SQUID could be used as a magnetometer, also measuring only one data point in the encoded spectrum corresponding to the z component of the magnetization. However, essentially any magnetometer could measure the z-magnetization and supply one point in the encoded signal, simplifying the data to a 1-D experiment although still preferably taken point by point.

It can be seen that the amplified signal scheme provides a modality for measuring miniscule NMR signals arising from small subject samples, in-vivo cells, and micro-devices like microfluidic chips. It would also allow the detection of small SPINOE effects in materials, which may be crucial in revealing solvent-solute interactions, surface properties in solid materials, and local structures like hydrophobic pockets in proteins and other complex molecules.

It can also be seen that this embodiment provides for measurement of Xe chemical shifts in samples at ultra-low fields for use as contrast agent in imaging and spectroscopy. The monitoring of diffusion, exchange, and imaging of Xe in the tissues surrounding the lung could be conducted by encoding in the lung and detecting outside of the body.

Similarly, this embodiment provides for analysis of noble gas-sample interactions that may provide selective imaging of samples. The enhanced signal may also allow the study of fundamental physics in isolated and single spin systems.

Accordingly, the embodiment shown in FIG. 4 with optically detected NMR/MRI signals provides a method of amplifying the Xe signal from samples over what is typically detected using a conventional NMR detection apparatus.

The present invention may be more particularly described in the following examples that are intended for illustrative purposes only, since numerous modifications, adaptations and variations to the apparatus and methods will be apparent to those skilled in the art.

EXAMPLE 1

A preliminary test of the concept of remote detection used an apparatus in which both an encoding coil and detection coil were controlled within the same NMR spectrometer with the same magnetic field and had a minimal travel distance between the encoding and detection coils. The high field encoding probe that was used contains two coils that are separated by 2 cm, center to center, and by a copper sheet, which serves as an rf shield. The encoding and detection coils were each controlled by a separate x-channel of a Varian Infinity Plus spectrometer tuned to 83.25 MHz.

Hyperpolarized $^{129}$Xe, polarized to 1–5%, was produced using a commercial polarizer from MITI. After the polarized $^{129}$Xe gas was produced, the flow was directed through the encoding and detecting coils sequentially and was later lost into the laboratory atmosphere or was alternatively returned to the polarizer. Gas flow rate was controlled using a pressure differential through a silver coated needle valve and an on-board flow meter. The gas was stopped during the pulse sequence using a TTL driven home built gas flow valve. The subject sample in the lower or encoding coil was a packed layer of Aerogel crystals. Aerogel is a low density silicate that allows $^{129}$Xe to freely pass through its lattice and also produces a chemical shift of about 25 ppm corresponding to bound $^{129}$Xe.

The advantages of remote detection are gained from the versatile use of different field strengths and sample locations. To show this experimental flexibility, a low field encoding of signal carriers that are then transferred to a high field remote detection apparatus was also built as schematically shown in FIG. 3. The $^{129}$Xe was polarized to 1–2% in a home built circular flow polarizer. The polarized gas is pushed through the ⅛ inch Teflon tubing using a magnetically driven re-circulation pump. An ASCO three way gas flow valve configured to be triggered from the spectrometer was used to redirect the flowing gas either through the magnets or back to the inlet of the polarizer, allowing an efficient mechanism to stop flow during the pulse sequence. The gas is preferably temporarily stopped during the encoding step in order to avoid a signal loss due to flow through gradient. Redirecting the flow to a bypass loop effectively stopped the polarized gas in the magnet loop. The polarizing gas mixture of Xe/N2/He was mixed with ratio 1/2/3 and a total pressure of 7 atm. The other details of the polarization process have been described previously.

The encoding magnet and probe were both home built. The magnet provided a homogeneous field of 70.1 Gauss with a current of 8.19 A applied. The probe was tuned correspondingly to a frequency of 83.3 kHz and its impedance matched to 50 ohms with a standard tank circuit. The pulses were gated and generated from a Hewlett Packard 3314A frequency generator and amplified to up to 20 $V_{p-p}$ by an Amplifier Research 75-Watt unity gain amplifier. With an 8 $V_{p-p}$ pulse, the experimental 90° time was about 48 μs. The three dimensional gradient coils were fixed on the outside of the magnet bore. This allowed the probe to be moved independently from the gradients magnets. The high field detection magnet was a 4.23 T super wide bore with a $^{129}$Xe frequency of 49.782 MHz. The home built imaging probe was controlled from the x-channel of a Chem Magnetics spectrometer.

The high field encoding and high field detecting apparatus generally shown in FIG. 2 described above was used to obtain a spectrum for comparison with a spectrum obtained from a direct measurement of the same sample and shown in FIG. 5. It was shown that the remote signal could be amplified by concentrating the xenon sample in the detection coil 32. It can be seen from the comparison in the high field experiment that a spectrum obtained point by point in a remote detector is essentially identical to the spectrum that is directly detected in the encoding NMR coils. The sample in the encoding coil 24 was an Aerogel sample with ~25 ppm chemical shift with respect to the Xe gas peak. The direct spectrum was recorded from the encoding coil 24 for comparison and had an absorbed peak signal to noise ratio of ~2:1. The remote spectrum had three peaks corresponding to the $^{129}$Xe gas peak, the absorbed phase peak and a DC offset peak that comes from $^{129}$Xe, which was not encoded in the encoding coil 24. The signal to noise ratio (S/N) of the absorbed peak in the remotely detected spectrum was found to be ~20:1. The amplification of signal between the two spectra can be attributed to an increased density of spins within the detection coil of the remote experiment. This was achieved by using a coil with a 10× improved filling ratio.

It was also seen that a large zero peak appeared in the 1D projection of the remote spectrum. After the $^{129}$Xe gas was encoded, it was moved from the encoding coil to the detecting coil. The encoded portion of the gas mixed with un-encoded gas during the travel time following the laws of gas flow and diffusion. Accordingly, the signal amplitude that was detected in the detection coil 32 was a mixture of un-encoded and encoded $^{129}$Xe. The encoded signal amplitude was modulated by the point by point encoding but the un-encoded signal is constant. After the Fourier transform was performed on the direct dimension data, the modulated signal appeared to have a large DC offset due to the un-encoded $^{129}$Xe that was mixed in from the flow. The DC-offset was removed computationally before processing the indirect dimension of FIG. 5. The remaining DC-offset peak in the spectrum reflected the degree to which the overall polarization changed over the course of the experiment.

It was also seen that the S/N of the remote spectrum was superior to the directly detected spectrum. The improvement in S/N can be attributed to the improvement in filling factor in the detection coil. The same volume of gas was encoded in each experiment but the filling factor was better in the remote detection because the gas fills the coil volume more completely. This principle can be used to improve the signal of any remotely detected signal in which the spin density of encoded gas is low. The signal can be amplified by increasing the density of spins in the detection coil 32.

EXAMPLE 2

Using an apparatus shown generally in FIG. 3, a low field encoding and high field detecting procedure was performed. In this procedure, two dimensional images were obtained from a sample and Xe gas that was encoded at 0.008 T and detected at 4 T. The experimental apparatus and pulse sequence were identical to that in Example 1 with the exception that frequency encoding gradients were added between the two encoding 90° pulses. The travel time was set to 10 seconds corresponding to a flow rate of ~0.6 ml/s.

In order for a remote image to be properly reconstructed in the detection coil, preferably all of the encoded gas will be detected in the detection coil. The processes of diffusion and flow allow the encoded sample to mix with un-encoded gas and to spatially spread out along the length of tubing. The total distance traveled is approximately 5 m, but the movement of the encoded sample is better measured in terms of travel time.

The traveling time $T_t$ is preferably determined by inverting the magnetization at the encoder 24 using an adiabatic sweep pulse and then measuring the time required for the inverted sample to flow to the detection coil 32. A longer $T_t$ allows more diffusion and mixing leading to lesser modulation of the amplitude and greater temporal spread of the encoded sample.

The $T_t$ of the gas sample being imaged in this example was between 10 seconds and 12.7 seconds. A single 90° pulse was applied to the gas flowing in the detection coil and an FID that represented the amplitude of the signal in a volume that resides for ~0.15 s in the detection coil was taken. This is called the detection time $T_d$. The encoded Xe sample takes a total of 2.7 s to pass through the detection coil, which means that eighteen, 90° pulses separated by a time $T_d$=0.15 s and averaged are necessary to acquire the encoded signal from the full image. The resolution of the image is improved by acquiring the entire encoded sample, but the S/N is improved by averaging only those $T_d$ that are strongly modulated.

Cycling the current through x and y direction gradient coils so as to produce eight 1D projections separated by 22.5° was performed. Each projection has a 1.23 mT/m gradient oriented along a proscribed angle and a 64 point FID, yielding a resolution of 1.2 mm. Images consisting of sixteen, sixty-four point 1D projections separated by 11.25° were obtained. The projection angles were formed by physically rotating the low field probe by integer multiples of 11.25°. All of the obtained image projections were zero-filled to 256 points and multiplied by a suitable apodization filter. In addition the projections were corrected for low field magnet drift by centering each projection using a Lorenzian fit.

Accordingly, it will be seen that this invention is an apparatus and method providing a sensitive technique for NMR/MRI imaging of polarized signal carrier molecules and allowing the spatial and temporal separation of signal encoding and detection steps permitting the conditions of each step to be optimized. Imaging in the presence of susceptibility gradients can be performed using low $B_0$ fields and low frequency signals and the encoded signal carriers can be moved to another location and detected in high fields. Signal to noise ratios can also be optimized by the physical compression or thermal condensation of signal carrier atoms producing a higher spin density and coil filling factor. Remote optical detection may also provide an amplification of the signal over conventional tuning coils.

Although the description above contains many specificities, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A remote NMR detection system, comprising:
    an encoder;
    a sample vessel interacting with said encoder;
    a sensor comprising a magnetically active-nucleus containing species, wherein said sensor is discharged into said sample vessel for encoding sample vessel environment information;
    means for producing a controlled supply of said sensor operably coupled to said sample vessel;
    means for detecting magnetic resonance spectra from said encoded sensor; and
    means for transferring encoded sensor from said sample vessel to said means for detecting magnetic resonance spectra.

2. A system as recited in claim 1, wherein said means for producing a supply of sensor comprises a laser polarizing optical pump.

3. A system as recited in claim 1, wherein said encoder comprises a high magnetic field NMR encoding spectrometer.

4. A system as recited in claim 1, wherein said encoder comprises a low magnetic field encoding coil and gradient set.

5. A system as recited in claim 1, wherein said means for detecting comprises:
    a detection chamber, said chamber enclosing a quantity of vaporized alkali metal; and
    an optical detector configured to detect changes in the polarization of said alkali metal.

6. A system as recited in claim 1, wherein said means for detection comprises a Superconducting Quantum Interference Device (SQUID).

7. A system as recited in claim 1, wherein said means for detection comprises an optical magnetometer using nonlinear Faraday rotation.

8. An apparatus as recited in claim 1, wherein said means for detection comprises a high magnetic field NMR spectrometer.

9. A system as recited in claim 1, wherein said means for transferring said encoded sensor comprises a pump and tubing interconnecting said sample vessel and said detector.

10. A system as recited in claim 1, further comprising:
    means for controlling the transfer of said encoded sensor from said sample vessel and to said detector.

11. A remote NMR detection system, comprising:
    an encoder;
    a sample vessel interacting with said encoder;
    a sensor comprising a magnetically active-nucleus containing species, wherein said sensor is discharged into said sample vessel for encoding sample vessel environment information; and
    a detector configured to receive signal from said encoded sensor from said sample vessel and to detect a signal from said encoded sensor.

12. A system as recited in claim 11, wherein said sensor comprises a Noble Gas.

13. A system as recited in claim 12, wherein said Noble gas comprises an isotope of Xenon.

14. A system as recited in claim 12, further comprising:
    transfer media mixed with said sensor.

15. A system as recited in claim 14, wherein said transfer media comprises a plurality of gases.

16. A system as recited in claim 14, wherein said transfer media comprises a plurality of liquids.

17. A system as recited in claim 14, wherein said transfer media is a liquid selected from the group of liquids consisting of water, saline water, isotonic buffers, lipids, lipid emulsions, organic solvents and fluorocarbon blood substitutes.

18. A system as recited in claim 11, further comprising:
    means for concentrating said sensor prior to detection by said detector.

19. A system as recited in claim 18, wherein said means for concentrating comprises a pump.

20. A system as recited in claim 11, further comprising:
means for circulating said sensor from said sample analysis vessel and to said detector.

21. A system as recited in claim 20, wherein said means for circulating said sensor comprises a pump and tubing interconnecting said sample vessel and said detector.

22. A system as recited in claim 20, further comprising:
means for controlling the circulation of said hyperpolarized sensor from said sample vessel and to said detector.

23. A system as recited in claim 11, further comprising:
means for generating a continuous supply of hyperpolarized sensor.

24. A system as recited in claim 11, wherein said encoder comprises a high magnetic field NMR encoding coil and gradient set.

25. A system as recited in claim 11, wherein said encoder comprises a low magnetic field encoding coil and gradient set.

26. A system as recited in claim 11, wherein said detector comprises a Superconducting Quantum Interference Device (SQUID).

27. A system as recited in claim 11, wherein said detector comprises an optical magnetometer using nonlinear Faraday rotation.

28. An apparatus as recited in claim 11, wherein said detector comprises a high magnetic field NMR spectrometer.

29. An apparatus as recited in claim 11, wherein said detector comprises an unshimmed high magnetic field NMR spectrometer.

30. A remote NMR detection system, comprising:
an encoder;
a sample vessel interacting with said encoder;
a hyperpolarized sensor, wherein said hyperpolarized sensor is discharged into said sample vessel for encoding sample vessel environment information; and
a detector configured to receive said encoded hyperpolarized sensor from said sample vessel and to detect a signal from said encoded hyperpolarized sensor.

31. A system as recited in claim 30, wherein said hyperpolarized sensor comprises a Noble Gas.

32. A system as recited in claim 31, wherein said Noble gas comprises an isotope of Xenon.

33. A system as recited in claim 30, further comprising:
transfer media mixed with said hyperpolarized sensor.

34. A system as recited in claim 33, wherein said transfer media comprises a plurality of gases.

35. A system as recited in claim 33, wherein said transfer media comprises a plurality of liquids.

36. A system as recited in claim 33, wherein said transfer media is a liquid selected from the group of liquids consisting of water, saline water, isotonic buffers, lipids, lipid emulsions, organic solvents and fluorocarbon blood substitutes.

37. A system as recited in claim 30, further comprising:
means for concentrating said hyperpolarized sensor prior to detection by said detector.

38. A system as recited in claim 37, wherein said means for concentrating comprises a pump.

39. A system as recited in claim 30, further comprising:
means for circulating said hyperpolarized sensor from said sample analysis vessel and to said detector.

40. A system as recited in claim 39, wherein said means for circulating said hyperpolarized sensor comprises a pump and tubing interconnecting said sample vessel and said detector.

41. A system as recited in claim 39, further comprising:
means for controlling the circulation of said hyperpolarized sensor from said sample vessel and to said detector.

42. A system as recited in claim 30, further comprising:
means for generating a continuous supply of hyperpolarized sensor.

43. A system as recited in claim 30, wherein said encoder comprises a high magnetic field NMR encoding coil and gradient set.

44. A system as recited in claim 30, wherein said encoder comprises a low magnetic field encoding coil and gradient set.

45. A system as recited in claim 30, wherein said encoder comprises a high magnetic field MRI encoding coil and gradient set.

46. A system as recited in claim 30, wherein said detector comprises:
a detection chamber, said chamber enclosing a quantity of vaporized alkali metal; and
means for optical detection of changes in the polarization of said alkali metal.

47. A system as recited in claim 30, wherein said detector comprises a Superconducting Quantum Interference Device (SQUID).

48. A system as recited in claim 30, wherein said detector comprises an optical magnetometer using nonlinear Faraday rotation.

49. An apparatus as recited in claim 30, wherein said detector comprises a high magnetic field NMR spectrometer.

50. A method for providing remote NMR spectroscopy comprising:
exposing a sample to a supply of signal carrier sensor; encoding said signal carrier sensor exposed to said sample; transferring said signal carrier sensor from said sample to a detector; detecting a signal from said encoded signal sensor; and obtaining a magnetic resonance data from said detected signals.

51. A method for providing remote NMR spectroscopy as recited in claim 50, further comprising:
concentrating said encoded signal carrier sensor prior to detection.

52. A method for providing remote NMR spectroscopy as recited in claim 51, wherein said concentration step comprises concentrating said encoded signal carrier sensor by condensation.

53. A method for providing remote NMR spectroscopy as recited in claim 50, further comprising:
averaging said detected signals.

54. A method for providing remote NMR spectroscopy as recited in claim 50, wherein said exposing step comprises exposing said sample to a controlled flow of said signal carrier sensor, wherein said signal carrier sensor comprises a hyperpolarized Noble gas.

55. A method for providing remote NMR spectroscopy as recited in claim 50, wherein said exposing step comprises exposing said sample to a continuous flow of a said signal carrier sensor, wherein said signal carrier sensor is a hyperpolarized Noble gas.

56. A method for providing remote NMR spectroscopy as recited in claim 54, wherein said hyperpolarized Noble gas comprises Xenon.

57. A method for providing remote NMR spectroscopy as recited in claim 54, wherein said sample is exposed to a mixture of hyperpolarized Noble gases.

58. A method for providing remote NMR spectroscopy as recited in claim 57, wherein said mixture of hyperpolarized Noble gases comprises a mixture of Xenon and Helium.

59. A method for providing remote NMR spectroscopy as recited in claim 58, wherein said mixture of hyperpolarized Noble gases comprises a mixture of Xenon, Helium, and an inert gas.

60. A method as recited in claim 59, wherein said inert gas comprises nitrogen gas.

61. A method for providing remote NMR spectroscopy as recited in claim 54, further comprising:
mixing said hyperpolarized Noble gas with a liquid prior to exposure to said sample.

62. A method for providing remote NMR spectroscopy as recited in claim 61, wherein said liquid is a liquid selected from the group of liquids consisting of water, saline water, isotonic buffers, lipids, lipid emulsions, organic solvents, and fluorocarbon blood substitutes.

63. A method for providing remote NMR spectroscopy as recited in claim 50, wherein said detection step comprises NMR coil detection.

64. A method for providing remote NMR spectroscopy as recited in claim 50, wherein said detection step comprises optical detection through alkali metal-noble gas spin exchange.

65. A method for providing remote NMR spectroscopy as recited in claim 50, wherein said detection step comprises an optical magnetometer using non-linear Faraday rotation detection.

66. A method for providing remote NMR spectroscopy as recited in claim 50, wherein said detection step comprises detection with a superconducting quantum interference device.

67. A method for providing remote NMR spectroscopy as recited in claim 50, wherein said encoding step comprises the steps:
placing said sample in a homogeneous magnetic field;
exposing said sample to said signal carrier sensor;
subjecting said sample and said signal carrier sensor to a plurality of RF pulses; and
transferring said RF pulsed signal carrier sensor to a detector.

68. A method for providing remote NMR spectroscopy as recited in claim 50, wherein said encoding step comprises the steps:
placing said sample in a homogeneous magnetic field;
exposing said sample to said signal carrier sensor for a first duration;
subjecting said sample and said signal carrier sensor to a first RF pulse;
waiting for a first period of time;
subjecting said sample and said signal carrier sensor to a second RF pulse;
waiting for a second period of time; and
transferring said exposed signal carrier sensor to a detector.

69. A method as recited in claim 68, wherein said first RF pulse comprises a 90+ pulse.

70. A method as recited in claim 68, wherein said second RF pulse comprises a 90+ pulse.

71. A method as recited in claim 68, wherein said homogeneous magnetic field differs from a field utilized in said detection.

72. A method as recited in claim 68, further comprising:
exposing said exposed signal carrier sensor to a third RF pulse in said detector.

* * * * *